United States Patent [19]

Andress, Jr.

[11] 4,240,803

[45] Dec. 23, 1980

[54] FUEL CONTAINING NOVEL DETERGENT

[75] Inventor: Harry J. Andress, Jr., Wenonah, N.J.

[73] Assignee: Mobil Oil Corporation, New York, N.Y.

[21] Appl. No.: 941,604

[22] Filed: Sep. 11, 1978

[51] Int. Cl.$^3$ ............................................... C10L 1/22
[52] U.S. Cl. ........................................... 44/63; 44/71;
   252/51.5 A
[58] Field of Search ................. 252/51.5 A; 44/71, 63

[56] References Cited

U.S. PATENT DOCUMENTS

| | | | |
|---|---|---|---|
| 3,172,892 | 3/1965 | Le Suer et al. | 252/51.5 A |
| 3,219,666 | 11/1965 | Norman et al. | 252/51.5 A |
| 3,223,495 | 12/1965 | Calvino et al. | 44/71 |
| 3,272,746 | 9/1966 | Le Suer et al. | 252/51.5 A |
| 3,281,428 | 10/1966 | Le Suer | 252/51.5 A |
| 3,445,386 | 5/1969 | Otto et al. | 252/51.5 A |
| 3,497,334 | 2/1970 | Gee et al. | 44/71 |
| 3,511,780 | 5/1970 | Neblett et al. | 44/71 |

FOREIGN PATENT DOCUMENTS 922831   4/1963   United Kingdom .

*Primary Examiner*—Patrick Garvin
*Assistant Examiner*—Raymond K. Covington
*Attorney, Agent, or Firm*—Charles A. Huggett; Raymond W. Barclay; Claude E. Setliff

[57] ABSTRACT

Fuel compositions are provided that contain an alkenyl-succinimide, where the alkenyl is derived from a mixture of $C_{16}$–$C_{28}$ olefins.

6 Claims, No Drawings

FUEL CONTAINING NOVEL DETERGENT

BACKGROUND OF THE INVENTION

1. Field of the Invention

The invention relates to liquid hydrocarbon fuel compositions. More particularly it relates to fuel compositions containing a detergent additive.

2. Description of the Prior Art

It is well known to those in this art that liquid hydrocarbon combustion fuels, such as fuel oils and gasolines, tend to exhibit certain deleterious characteristics, either after long periods of storage or under actual operational conditions. Gasolines, for example, in operational use tend to deposit sludge and varnish at various points in the power system, including carburetor and intake valves. It is desirable, therefore to find a means for improving liquid hydrocarbon fuels by lessening their tendency to leave such deposits.

Recent interest in the use of detergents for liquid hydrocarbon fuels has lead to the employment of non-metallic compounds. The advantageous feature of these non-metallic detergents is that they do not leave ashy deposits in an engine as do the metallic detergents. Such detergents include alkyl-substituted organic compounds, some of them polymeric in nature, one particular class containing amide or imide groups. The optimum activity of many of these detergents appears to be at low or moderate temperatures only.

U.S. Pat. Nos. 3,172,892; 3,219,666; 3,272,746; 3,281,428 and 3,445,386 are directed broadly to polyalkenylsuccinictype ashless additives. The first four patents disclose additives in which the alkenyl group is derived from the poly-$C_4$ olefins. The last patent teaches an alkenyl derived from polypropylene having a molecular weight of from about 500 to about 3000. It also teaches the use of the additive disclosed therein as a fuel detergent.

U.S. Pat. No. 3,649,229 teaches a fuel containing a detergent amount of a Mannich base product made using, among other reactants, an alkenylsuccinic compound.

SUMMARY OF THE INVENTION

The invention provides a liquid hydrocarbon fuel composition comprising fuel and a detergent amount of an alkenylsuccinimide prepared by reacting an alkenylsuccinic acid or anhydride, wherein the alkenyl is derived from a mixture of $C_{16}$-$C_{28}$ olefins, with a polyalkylene polyamine of the formula $$NH_2-(RNH)_nR-NH_2$$

wherein R is alkylene having from 1 to 5 carbon atoms and n is from 0 to 10.

DESCRIPTION OF SPECIFIC EMBODIMENTS

The alkenylsuccinic anhydride can be made in accordance with a prior art process involving the thermal condensation of an olefin mixture with maleic anhydride. This is conveniently carried out at from about 150° C. to about 250° C., preferably about 175° C. to 225° C.

It has been found that, for unexpected effectiveness as a liquid hydrocarbon detergent, it is essential that the alkenyl group attached to the succinic acid or anhydride be derived from a mixture of $C_{16}$-$C_{28}$ olefins. This essential olefin mixture is the bottoms from an olefin oligomerization, and such mixture will have the following composition:

TABLE 1

| Ingredient | % By Wt. | Other |
|---|---|---|
| Olefin (chain length) | | |
| $C_{16}$ | 2, maximum | |
| $C_{18}$ | 5–15 | |
| $C_{20}$ | 42–50 | |
| $C_{22}$ | 20–28 | |
| $C_{24}$ | 6–12 | |
| $C_{26}$ | 1–3 | |
| $C_{28}$ | 2, maximum | |
| Alcohol | 10, maximum | |
| Paraffin | 5, maximum | |
| Iodine No. | | 74, minimum |
| Peroxide | | 10 ppm, maximum |
| Olefin types by NMR | | |
| Vinyl | 28–44 | |
| Branched | 30–50 | |
| Internal | 26–42 | |

Because of the source of the olefin mixture, one does not always get the same product from successive batches. However, each mixture will have a composition falling within the ranges stated and will be equally effective for use in this invention. While the exact composition is not known, the number average molecular weight can be determined so proportions of reactant can be readily determined.

As has been mentioned, the polyalkenylsuccinic anhydride or acid is reacted with a polyalkylene polyamine of the structure $$NH_2-(RNH)_nR-NH_2$$

wherein R is an alkylene having from 1 to 5 carbon atoms, inclusive, and n is from 0 to 10, inclusive. Suitable polyamines include methylene diamine, ethylene diamine, diethylene triamine, dipropylene triamine, triethylene tetramine, tetraethylene pentamine, pentamethylene hexamine, hexaethylene heptamine, undecaethylene dodecamine, and the like. One series of reactions, showing one possible product, is as follows:

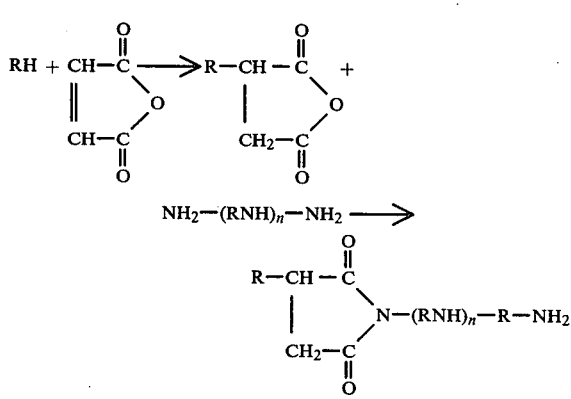

The reaction mixture may contain from 1 mole of the anhydride per mole of the amine, or it may have an amount of anhydride equivalent to the total >NH functions in the amine, i.e. up to 12 moles of anhydride per mole of amine.

In general, the invention contemplates the use of from about 0.00001 percent of about 15 percent of the additive by weight of the fluids disclosed herein. Preferably, the concentration in hydrocarbon fuels will preferably be within the range of from about 0.000025 percent to about 0.05 percent by weight thereof. Expressed in another way for the hydrocarbon fuel, the overall range will be from about 0.1 lb. to about 200 lbs. per 1,000 barrels of fuel, and the most preferred will range from about 1 pound to about 10 pounds per 1,000 barrels.

A field of specific applicability of the present invention is in the improvement of organic liquid compositions in the form of petroleum distillate fuel oils having an initial boiling point from about 75° F. to about 135° F. and an end boiling point from about 250° F. to about 1,000° F. It should be noted, in this respect, that the term "distillate fuel oils" is not intended to be restricted to straight-run distillate fractions. These distillate fuel oils can be straight-run distillate fuel oils, catalytically or thermally cracked (including hydrocracked) distillate fuel oils, or mixture of straight-run distillate fuel oils, naphthas and the like, with cracked distillate stocks. Moreover, such fuel oils can be treated in accordance with well-known commercial methods, such as acid or caustic treatment, hydrogenation, solvent refining, clay treatment, and the like.

The distillate fuel oils are characterized by their relatively low viscosity, pour point and the like. The principal property which characterizes their contemplated hydrocarbons, however, is their distillation range. As hereinbefore indicated, this range will lie between about 75° F. and about 1,000° F. Obviously, the distillation range of each individual fuel oil will cover a narrower boiling range, falling nevertheless, within the above-specified limits. Likewise, each fuel oil will boil substantially, continuously, throughout its distillation range.

Particularly contemplated among the fuel oils are Nos. 1, and 3 fuel oils, used in heating and as Diesel fuel oils, gasoline, turbine fuels and the jet combustion fuels, as previously indicated. The domestic fuel oils generally conform to the specifications set forth in ASTM Specification D396-48T. Specifications for Diesel fuels are defined in ASTM Specification D975-48T. Typical jet fuels are defined in Military Specification MIL-F-5624B.

Having described the invention broadly, the following specific examples will illustrate it. It should be understood that the Examples are illustrative only and are not intended to limit the invention.

EXAMPLE 1

A mixture of 600 grams (2.0 mols) of the above-described olefin mixture comprising

| Olefin (chain length) | % By Wt. |
|---|---|
| $C_{16}$ | 2. max. |
| $C_{18}$ | 5–15 |
| $C_{20}$ | 42–50 |
| $C_{22}$ | 20–28 |
| $C_{24}$ | 6–12 |
| $C_{26}$ | 1–3 |
| $C_{28}$ | 2. max. |
| Alcohol | 10. max. |
| Paraffin | 5. max. |
| Olefin Types by N.M.R. | |
| Vinyl | 28–44 |
| Branched | 30–50 |

| Olefin (chain length) | % By Wt. |
|---|---|
| Internal | 26–42 | and 198. grams (2.0 mols) of maleic anhydride was stirred at about 200°–210° C. for seven hours and at about 235°–240° C. for three hours to form the alkenylsuccinic anhydride.

A mixture of 170 grams (0.9 mol) of tetraethylene pentamine and 500 ml of toluene diluent was added to the alkenylsuccinic anhydride at 75° C. The mixture was gradually refluxed to about 175° C. and held until the evolution of water ceased. The final product was obtained by topping under reduced pressure.

EXAMPLE 2

A mixture of 400 grams (1.0 mol) of the alkenylsuccinic anhydride (prepared according to Example 1) and 73 grams (0.5 mol) of diethylene triamine was diluted with 250 ml toluene and refluxed to about 175° C. until the evolution of water ceased. The final product was obtained by topping under reduced pressure.

EXAMPLE 3

A mixture of 349 grams (0.5 mol) of alkenylsuccinic anhydride and 47.2 grams (0.25 mol) of tetraethylene pentamine was refluxed with toluene diluent to about 200° C. until evolution of water ceased. Topping under reduced pressure gave the final product. The alkenylsuccinic anhydride used in this example was made by dimerizing the olefin mixture of Example 1 by (1) adding n-butanol to such mixture and bubbling in boron trifluoride at about 85° C. for about 1 hour and then (2) reacting the resulting dimer with maleic anhydride under conditions similar to those described in Example 1.

EXAMPLE 4

A mixture of 675 (0.5 mol) of a polyisobutenylsuccinic anhydride and 47.2 grams (0.25 mol) of tetraethylene pentamine was stirred at 180° C. until the evolution of water ceased. The product represents a typical fuel detergent.

EVALUATION OF PRODUCTS

Carburetor Detergency Test

The deposit-forming tendencies of a fuel are determined in an 8-hour engine test. This accelerated test, when run on fuels that contain no detergents, produces an amount of deposit equivalent to the amount observed in 4,000 miles of operation in field tests on taxicab fleets. A Ford 240 cu. in. engine is equipped with notched rings to increase the amount of blowby and with a glass throttle body section. The engine is operated for 8 hours, using the fuel under test, at alternate idling and running cycles. In the idle cycle, the engine is run at idling speed of 400 rpm with no load, for 5 minutes. Then for 1 minute, the engine is run at a speed of 2,500 rpm under a load of 30 BPH and at 9.4 in. of mercury manifold pressure. During the running cycle, the blowby and part of the exhaust are released into the carburetor air intake during the idling cycle. After 8 hours' operation at alternate run and idle, the carburetor is examined and rated as to the amount of deposit in the throttle throat. The table below summarizes the data obtained.

TABLE 2

Carburetor Detergent Test

Ford 240 cu. in. Engine

The inhibitors were blended in a gaoline comprising 40% catalytically cracked component, 40% catalytically reformed component, and 20% alkylate of about 90°–410° F. boiling range.

| Compound | Conc. Lbs./ 1,000 Bbls. | Reduction in Deposits, % |
|---|---|---|
| Base Fuel | 0 | 0 |
| Base Fuel + Ex. 1 | 5 | 62. |
|  | 10 | 79. |
| Base Fuel + Ex. 2 | 10 | 50. |
| Base Fuel + Ex. 3 | 5 | 30. |
|  | 10 | 60. |
| Base Fuel + Ex. 4 | 10 | 15. |

I claim:

1. A liquid hydrocarbon fuel compsition comprising fuel and a detergent amount of an alkenylsuccinimide prepared by reacting, at a temperature within the range of from about 150° C. to about 250° C., an alkenylsuccinic acid or anhydride, wherein the alkenyl is derived from a mixture of olefins having the composition:

| Ingredient | % By Wt. | Other |
|---|---|---|
| Olefin |  |  |
| $C_{16}$ | 2, maximum |  |
| $C_{18}$ | 5–15 |  |
| $C_{20}$ | 42–50 |  |
| $C_{22}$ | 20–28 |  |
| $C_{24}$ | 6–12 |  |
| $C_{26}$ | 1–3 |  |
| $C_{28}$ | 2, maximum |  |
| Alcohol | 10, maximum |  |
| Paraffin | 5, maximum |  |
| Iodine No. |  | 74, minimum |
| Peroxide |  | 10 ppm, maximum |
| Olefin types |  |  |
| Vinyl | 28–44 |  |
| Branched | 30–50 |  |
| Internal | 26–42 |  | with a polyalkylamine polyamine of the formula $$NH_2-(RNH)_nR-NH_2$$

wherein R is alkylene having from 1 to 5 carbon atoms and n is from 0 to 10.

2. The composition of claim 1 wherein the fuel is gasoline.

3. The composition of claim 1 wherein the polyamine is tetraethylene pentamine.

4. The composition of claim 1 wherein the polyamine is diethylene triamine.

5. The composition of claim 1 wherein there is present during reaction from 1 to 12 moles of anhydride or acid per mole of polyamine.

6. The composition of claim 1 containing from about 0.1 lb. to about 200 lbs. of alkenylsuccinimide per 1000 barrels of fuel.

* * * * *